US008245335B2

(12) United States Patent
Shvartsberg et al.

(10) Patent No.: US 8,245,335 B2
(45) Date of Patent: Aug. 21, 2012

(54) SUPPORT COMPONENT FOR USE IN IMAGING BY MAGNETIC RESONANCE AND X-RAY (75) Inventors: Alexander Shvartsberg, Winnipeg (CA); Labros Petropoulos, Chagrin Falls, OH (US); Victoria D. M. Hornblower, Winnipeg (CA)

(73) Assignee: Imns Inc., Wpg, MB (CA)

( * ) Notice: Subject to any disclaimer, the term of this patent is extended or adjusted under 35 U.S.C. 154(b) by 552 days.

(21) Appl. No.: 12/413,953

(22) Filed: Mar. 30, 2009

(65) Prior Publication Data
US 2010/0249575 A1 Sep. 30, 2010

(51) Int. Cl.
A61B 6/04 (2006.01)
A61G 13/00 (2006.01)
A61G 13/12 (2006.01)

(52) U.S. Cl. ......... 5/601; 5/600; 5/622; 5/621; 378/208; 378/209

(58) Field of Classification Search .............. 5/601, 600, 5/621–624; 378/209, 208
See application file for complete search history.

(56) References Cited

U.S. PATENT DOCUMENTS

| 4,566,445 | A | * | 1/1986 | Jelsma et al. | 606/242 |
| 4,595,899 | A | | 6/1986 | Smith | |
| 4,698,837 | A | * | 10/1987 | Van Steenburg | 378/208 |
| 4,926,457 | A | * | 5/1990 | Poehner et al. | 378/208 |
| 4,956,885 | A | * | 9/1990 | Alich et al. | 378/209 |
| 5,099,846 | A | | 3/1992 | Hardy | |
| 5,291,890 | A | | 3/1994 | Cline | |
| 5,713,357 | A | | 2/1998 | Meulenbrugge | |
| 5,735,278 | A | | 4/1998 | Hoult et al. | |
| 5,771,513 | A | * | 6/1998 | Kirchgeorg et al. | 5/601 |
| 5,865,780 | A | | 2/1999 | Tuite | |
| 5,950,627 | A | * | 9/1999 | Bologovsky et al. | 128/869 |
| 5,996,149 | A | * | 12/1999 | Heimbrock et al. | 5/601 |
| 6,101,239 | A | | 8/2000 | Kawasaki | |
| 6,151,732 | A | * | 11/2000 | Heimbrock et al. | 5/601 |

(Continued)

FOREIGN PATENT DOCUMENTS
DE 39 31 854 4/1991
(Continued)

OTHER PUBLICATIONS

Pro-Med Instruments GMBH: "DORO Radiolucent Headrest System FDA K063494", USA, May 21, 2007—see pp. A1-4 to A1-6.

Primary Examiner — Robert G Santos
(74) Attorney, Agent, or Firm — Adrian D. Battison; Ade & Company Inc (57) ABSTRACT A structural support component such as a head clamp for use in imaging of a part of a patient using Magnetic Resonance and X-ray imaging is formed of different materials each of which has an Aluminum equivalence factor of less than 10 mm and generally less than 6 mm and is arranged such that the presence of the structural support component in an imaging zone of a magnetic resonance imaging system when generating the image does not generate any visually determinable distortion in the image. The materials can be epoxy resin combined with a glass fiber substrate for easily machined parts, polyphenylene sulphide with random fiber reinforcement using glass fibers for high wear parts and polyurethane foam or Polymethacrylimide foam shaped to form a required member and covered on its outer surface with a layer formed from aramid fibers for elongate parts.

11 Claims, 5 Drawing Sheets

U.S. PATENT DOCUMENTS

| | | |
|---|---|---|
| 6,385,480 B1 | 5/2002 | Bachus |
| 6,640,364 B1 * | 11/2003 | Josephson et al. ............ 5/601 |
| 6,658,085 B2 | 12/2003 | Sklebitz |
| 6,754,519 B1 | 6/2004 | Hefetz |
| 6,782,571 B1 * | 8/2004 | Josephson et al. ............ 5/601 |
| 6,812,700 B2 | 11/2004 | Fahrig |
| 6,961,606 B2 | 11/2005 | DeSilits |
| 6,975,895 B1 | 12/2005 | Pelc |
| 7,484,253 B1 * | 2/2009 | Coppens ........................ 5/601 |
| 7,742,562 B2 * | 6/2010 | Weber ........................ 378/68 |
| 2005/0075650 A1 | 4/2005 | Dinkler |
| 2006/0185087 A1 * | 8/2006 | Coppens et al. ............ 5/601 |
| 2006/0239524 A1 | 10/2006 | Desh |
| 2008/0042076 A1 | 2/2008 | Miller et al. |
| 2008/0072381 A1 | 3/2008 | Rolfes |
| 2009/0264938 A1 | 10/2009 | Bailey et al. |
| 2010/0010337 A1 | 1/2010 | Hagen et al. |
| 2010/0192303 A1 * | 8/2010 | Miller et al. .................. 5/622 |
| 2010/0249575 A1 * | 9/2010 | Shvartsberg et al. ......... 600/415 |

FOREIGN PATENT DOCUMENTS

| | | |
|---|---|---|
| JP | 4183446 | 6/1992 |
| JP | 05344964 | 12/1993 |
| WO | WO 2007/065013 | 6/2007 |
| WO | WO 2007014233 A1 | 12/2007 |

* cited by examiner

Fig 3

SUPPORT COMPONENT FOR USE IN IMAGING BY MAGNETIC RESONANCE AND X-RAY

This invention relates to a support component for use in imaging by magnetic resonance (MRI) and X-Ray of a patient.

BACKGROUND OF THE INVENTION

With MRI, a high field magnet, typically superconducting, is arranged in a torus configuration (like a donut) and with the patient lying down inside the magnet on a table where the magnetic field allows a pulsed and sequenced magnetic and EM field to probe the body to produce images, which allow the trained radiologist to determine with high probability the anatomy of the patient. MRI is sometimes performed using contrast agents introduced to the patient to provide even better contrast between different tissue types. MRI techniques are very good at detecting the anatomical location of different diseases, for example, tumours.

In U.S. Pat. No. 5,735,278 (Hoult et al) issued Apr. 7, 1998, disclosed a medical procedure where a magnet is movable relative to a patient and relative to other components of the system. The moving magnet system allows intra-operative MRI imaging to occur more easily in neurosurgery patients, and has additional applications for liver, breast, spine and cardiac surgery patients.

In Published PCT Application WO07147233A1 of the present Applicants published Dec. 27, 2007 and entitled ROTATABLE INTEGRATED SCANNER FOR DIAGNOSTIC AND SURGICAL IMAGING APPLICATIONS is disclosed an improvement to the above patent in which an additional rotational movement of the magnet is allowed.

A scanning system is known in which the patient is moved from an X-ray imaging system to an MR imaging system by transferring the patient from one imaging system to the other, for example, on a moveable table. The MR scanner is used to provide information complementary to that obtained using X-ray. It can be used, for example, to perform a baseline assessment prior to intervention as well as to perform a post-intervention assessment. Such an assessment may include perfusion and viability studies of the heart or of the brain.

U.S. Pat. No. 5,713,357 (Meulenbrugge) issued Feb. 3, 1998 and related U.S. Pat. No. 5,807,254 both of Phillips shows a combination of an X-ray system and an MRI system. The system is not for intra-operative uses and the magnet is not a cylinder. The magnet is not moved. The X-ray is moved side to side in FIG. 2. The patient is moved in FIG. 1.

U.S. Pat. No. 6,101,239 (Kawasaki) issued Aug. 8, 2000 to Hitachi provides an X ray and MRI operating simultaneously at the same location and methods to operate them in a timed manner to avoid interference. However this arrangement is not suitable for interventions by the medical team since the presence of the machines restricts access to the patient.

U.S. Pat. No. 6,385,480 (Bachus) issued May 7, 2002 of Siemens discloses what they call an angio-MR system where the radiographic angio-system cooperates with the MR system. There is provided a moving patient table which transfers the patient from the X-ray system at one location to the MRI at a second location.

US Patent Application 2006/0239524 (Desh) published Oct. 26, 2006 of Siemens relates to diagnosis and treatment of cardiac diseases using MRI and X-ray. This is directed to a method of combining the images to analyze the diagnosis.

U.S. Pat. No. 6,975,895 (Pelc) issued Dec. 13, 2005 to Leland Stanford University provides a modified X ray tube for use in magnetic fields of an MRI system.

U.S. Pat. No. 6,812,700 (Fahrig) issued Nov. 2, 2004 of Leland Stanford University discloses a related system in which the perturbations in the magnetic field of the MRI caused by the X-ray system are compensated.

U.S. Pat. No. 6,658,085 (Sklebitz) issued Dec. 2, 2003 of Siemens discloses a system in which current for the coils generating the magnetic field of the MRI is calculated to reduce stray fields in the area of the X-ray system.

U.S. Pat. No. 5,865,780 (Tuite) issued Feb. 2, 1999 of SDGI Holdings discloses a device for engaging and holding the body of the patient during procedures in MRI and X-ray imaging.

U.S. Pat. No. 4,595,899 (Smith) issued Jun. 17, 1986 to Leland Stanford University provides an MRI system.

U.S. Pat. No. 5,099,846 (Hardy) issued Mar. 31, 1992 relates to combining images from different imaging modalities and is primarily about the software for combining the images such as X-ray and NMR.

U.S. Pat. No. 6,754,519 (Hefetz) issued Jun. 22, 2004 to Elgems discloses two imaging systems such as CT and MRI where the two systems are mounted on a common rail system for rolling movement from a common position to a spaced position.

U.S. Pat. No. 5,291,890 (Cline) issued Mar. 8, 1994 to GE discloses a patient heat treatment system where the heat is detected using an MRI.

U.S. Pat. No. 6,961,606 (DeSilits) issued Nov. 1, 2005 to Phillips discloses two imaging systems such as CT and PET where the two systems are mounted on a common rail system for rolling movement from a common position together for common scanning of the patient to a spaced apart position.

German patent application 39 31 854 of Muller published Apr. 4, 1991 discloses an NMR apparatus using a laser coagulation stereotactic system.

Japanese application 05344964 of Toshiba shows a combination of an X-ray system and an MRI system. This is application is filed only in Japan and provides what is apparently a crude system.

Japanese patent application 4183446 published Jun. 30, 1992 by Res Dev Corp of Japan discloses the use of MRI and X-Ray in a common apparatus.

One element which must be designed for use with a combined imaging system of the type described above is that of the patient support table and components for providing support which are used during the procedures in the MR and X-ray imaging.

Typically during imaging and non-surgical intervention, the patient is merely resting on a suitable support surface which can be just the table or a table with extensions for holding the head or other extremities.

However during surgical procedures it is necessary in many cases to provide structural support components which hold a body part such as the head of the patient stationary during the imaging and during the procedures which follow the imaging.

Such structural support components when used in X-ray imaging systems are typically formed from a material commonly known as Novotex which is supplied by Pro-Med Instruments Inc, Manufacturing and Distribution of Surgical Products and is formed of a phenolic resin reinforced by cotton fibers. This is selected because it has a low absorption factor for X-rays which is measured as an Aluminum equivalence factor and this is typically of the order of 4 mm for 10 mm of material. Usually devices require much thicker material, as much as 25 to 30 mm which takes the Aluminum equivalence factor to 8 to 10 mm.

Such materials including particularly the Novotex material are considered to be MR compatible in that they are non-ferromagnetic so that they can be placed in the magnetic field and they are non-electrically conductive so that they do not affect the radio frequency fields. Novotex also provides the necessary adequate physical characteristics including strength and hardness so that it is to be expected that Novotex can be used for constructions to be used in both MR and X-ray imaging.

SUMMARY OF THE INVENTION

It is one object of the present invention to provide a support component which can be used in a combined MR and X-ray imaging system of the type described above.

According to a first aspect of the invention there is provided a structural support component for use in imaging of a part of a patient using Magnetic Resonance and X-ray imaging;

the structural support component being formed of one or more materials each of which has an Aluminum equivalence factor for a sample of 10 mm in thickness of less than 10 mm;

the structural support component being arranged such that the presence of the structural support component in an imaging zone of a magnetic resonance imaging system when generating the image does not generate any visually determinable distortion in the image.

Preferably the Aluminum equivalence factor of less than 8 mm and more preferably of the order of 5 to 6 mm.

Preferably the component is formed of two different materials where the materials have different physical characteristics.

Preferably one of the materials is harder is and is used to form wear parts where two separate parts are butting.

Preferably one of the materials is more rigid is and is used to form elongate bars.

Preferably the component is formed of three different materials where the materials have different physical characteristics, with a first material selected to form an elongate bar, a second material selected to form machined end portions of the bar and a third material selected to form wear parts attached to the end portions.

Preferably one of the materials is an epoxy resin combined with a glass fabric substrate.

Preferably said epoxy resin system combined with a glass fabric substrate is used for machined parts of the component.

Preferably one of the materials is a polyphenylene sulphide with random fiber reinforcement using glass fibers.

Preferably the polyphenylene sulphide with random fiber reinforcement using glass fibers is used to form wear parts.

Preferably one of the materials is a polyurethane foam shaped to form a required member and covered on its outer surface with a layer formed from aramid fibers coated with a heat curable resin.

Preferably the polyurethane foam shaped covered on its outer surface with a layer formed from aramid fibers is used to form elongate bars.

According to a second aspect of the invention there is provided a structural support component for use in imaging of a part of a patient using Magnetic Resonance and X-ray imaging;

the structural support component being formed of two or more different materials each of which has for a sample of 10 mm in thickness an Aluminum equivalence factor of less than 10 mm;

the structural support component being arranged such that the presence of the structural support component in an imaging zone of a magnetic resonance imaging system when generating the image does not generate unacceptable distortion in the image.

wherein the component is formed of two different materials where the materials have different physical characteristics.

According to a third aspect of the invention there is provided a structural support component for use in imaging of a part of a patient using Magnetic Resonance and X-ray imaging wherein the part is formed from epoxy resin combined with a glass fabric substrate.

According to a fourth aspect of the invention there is provided a structural support component for use in imaging of a part of a patient using Magnetic Resonance and X-ray imaging wherein the part is formed from polyurethane foam or polymethacrylimide (PMI) foam shaped to form a required member and covered on its outer surface with a layer formed from aramid fibers coated with a heat curable resin.

The structural support member can comprise a selected one of a series of devices, such a head fixation, head supports, retractors, imaging guide system reference plates and plates holders using both with Magnetic Resonance Imaging systems and Radiological (involving X-Ray) equipment. The member when formed of the above materials, have no influence on the final image, obtained by those systems. In order to get this, the material has neither ferromagnetic component (that might affect the constant field of the Magnetic Resonance Imaging system) nor other components that have any electrical conductivity (that might affect the RF field of the Magnetic Resonance Imaging system). From radiological point of view, the material has a relatively low number for Aluminum equivalence factor, only then is it possible to achieve clear X-ray imaging (taken through this material), which has low signal to noise ratio and without increasing X-ray power.

Using one of those materials or as a combination of them in fabrication of the MRI compatible and radiolucent type of Neuro surgical or interventional devices allows obtaining good images with no artifacts in the MRI and X-ray imaging systems, without compromising normal surgical procedures (e.g. moving the patient, changing tools and etc.), which will benefit to overall patient safety and procedural workflow.

The materials to be used include
  a) Garolite G10/FR4 which is a glass cloth laminate with epoxy resin binder;
  b) POLYPHENYLENE SULFIDE (PPS) mixed with nonwoven random fibreglass,
  c) Composite of the Aramid (Kevlar) with polyurethane foam or polymethacrylimide (PMI) foam inside.

The materials can be used for:

Head fixation device links, skull clamps and swivel adaptors: those devices usually use for patient positioning and fixation during open scalp Neuro surgical operations and cervical spine surgeries.

Table HFD adaptors: those devices use to interface between head fixation device and OR table.

Head supports: those devices usually use for patient positioning during open scalp Neuro surgical operations OR table side rail fittings: to interface between side rails and OR table.

Cervical spine supports: to support patient neck during cervical spine surgeries.

Head frames for stereotactic navigation: for intracranial tumors, invasive stereotactic frames screwed into the calvaria have been used for accurate insertion of iodine seeds and brain navigation.

Stereotactic tower apparatus: this apparatus comprises a rigid half circular head clamp, three fixation pins to firmly secure the clamp to the patient's skull, a connector to firmly secure the clamp to a surgical table on which the patient rests, an articulated arm including clampable joints, secured to the head clamp in one of several possible positions and a double chuck secured to the distal end of the articulated arm.

Imaging grids and grid holders: used for navigation purposes (imaging, radiation therapy) in different types of tumor locations (breast, prostate and etc.) Image guided system reference plates and plate holders: used for navigation purposes in brain Neuro surgery.

Interventional cardio vascular application package for use with both MR and Angio suites: used in combined Angio/Neuro suites.

Table top
Head Holder
Table extension board
Arm boards
Cardiac coil enclosure

Interventional and operational table top for use with both MR and Angio suites: used in combined Angio/Neuro suites.

Neuro surgical table for use with MR suite and mobile/stationary X-ray equipment: used as a part of Neuro suites.

DETAILED DESCRIPTION

Figure 1:
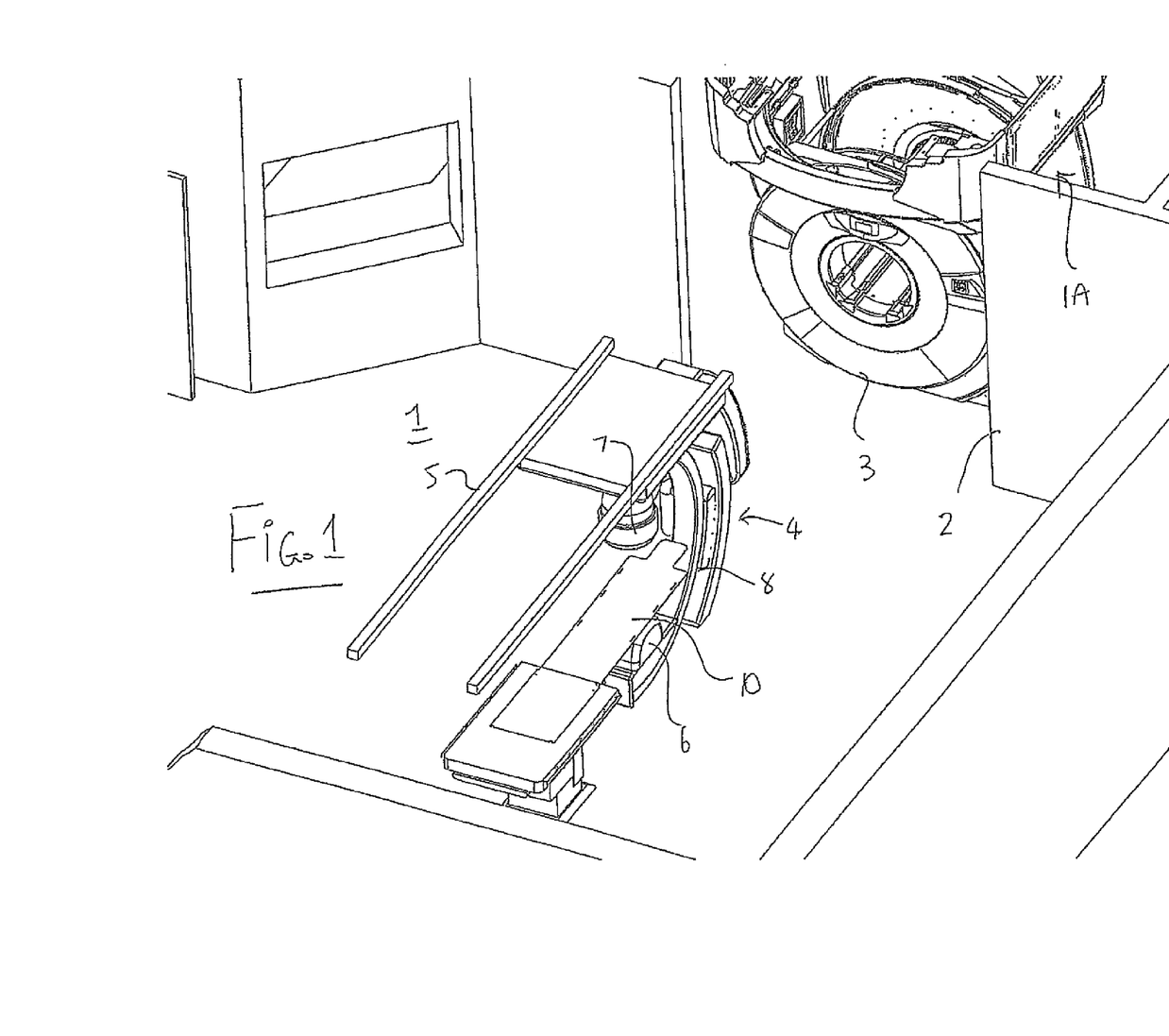
FIG. 1 is an isometric view of an Angiography room showing a patient table, an MRI magnet movable into a position for imaging the patient on the table and an arrangement for moving an X-Ray system.

In FIG. 1 is shown an arrangement for carrying out Magnetic Resonance Imaging and X-ray imaging of a patient while the patient remains stationary on a patient support table. The arrangement provides a room 1 in which is mounted a patient support table 10 with doors 2 at one side of the room for entry into the room of the magnet 3 of an MR imaging system from a magnet bay 1A. The room contains an X-ray imaging system 4 mounted on rails 5 and includes an X-ray transmitter 6 and receiver 7 mounted on a C-shaped support 8. The X-ray system is of a conventional construction commercially available from a manufacturer such as Siemens. The table 10 described and illustrated herein is used in an arrangement where the patient remains in position on the table while imaging is effected using MRI and X-ray.

Additional unique multi-room layouts, configurations and applications are possible when a rotating MRI system is designed. In this case, the following multi-room configurations are used as examples to illustrate the variety of applications which are possible, with all of these applications being financially beneficial to the healthcare industry.

The magnet system 3 moves into a room within 1 minute, and the doors 2 open within seconds, so the limiting factor on effectiveness of usage of the magnet system is providing the patients into and out of the room, prepping the patients if required, and discussing the imaging with the patients. It is known that a reasonable amount of time per imaging event is 60 minutes, and therefore the movement of the MRI scanner into and out of a room is not the limiting time value. As well, the efficiency of a multi-room system becomes more difficult to schedule as the need for both diagnostic and interventional procedures occurs. The following configurations are now possible:

A three room diagnostic configuration in which the central magnet holding bay 1A houses the magnet and the diagnostic patients are organized in the three rooms including the room 1 and a further room not shown beyond the bay 1A. The doors 2 to room 1 open, the magnet holding bay 1A becomes part of room 1. When the magnet moves to the second room, the magnet may not move but may extend its diagnostic table, the patient lies on the diagnostic table, imaging is performed, no need to do intervention is found, the patient exits the diagnostic table and the magnet moves back into the holding bay, ready for use by one of the other rooms. The magnet then may draw in its table, rotates to the doors for that room, and the process for the other room begins. In this case, the magnet does not move in a translational direction, such as on rails, but simply rotates.

A two room system is in the corner of the hospital. In this case, the magnet both rotates and translates. There is a central magnet holding room, with doors in each of the two 90 degree directions, and the magnet can rotate its diagnostic table in whichever direction is required, or can rotate to allow the opposite end of the magnet to enter the room first. This approach allows existing diagnostic functionality and applications to be used in either room, or allows both rooms to serve as intra-operative rooms without any significant change to magnet controls and monitoring. This two room corner system cannot be done without a rotating magnet.

The system can be suspended from the ceiling or mounted on a floor mounted bearing, with either system providing rotation of the magnet. The MRI system may also be suspended from the ceiling on rails, such that it can also be translated in space using the rail system. The rotational mechanism can either be located between the magnet and the rails, or above the rails. The below track and above track rotators have different properties for different configurations. The below track rotator allows for easiest upgrade of existing sites, whereas the above track rotator works like a roundhouse in a railway yard, in that the rail, MRI system and all associated systems are rotated.

Turning now to the arrangement including the X-ray system which cooperates with the moving magnet described above, the system consists of the movable magnet integrated with an X-ray system such that the patient can be imaged by either modality on the same table. The patient does not move.

The MR is a high-field horizontal or vertical type of magnet system that moves on overhead rails between the two or more rooms as described above. In the system described, one or more of these rooms contains an X-ray system, either a single-plane or a biplane. When the magnet is moved out of the X-ray examination room and a set of RF and X-ray shielded doors is closed, the examination room functions as a conventional X-ray lab and can be used with conventional equipment. In particular, X-ray guided interventions may be performed.

The arrangement may be used in a typical three room configuration with the Angiography Room (AR) on the left, a Diagnostic Room (DR) in the middle, and an Operating Room on the right. The magnet moves on overhead rails between the rooms and can image in each.

When MR imaging is required, the X-ray equipment is safely stowed, the doors open, and the magnet is brought into the room over the patient on the table. The RF shield encompasses the AR so all the equipment in the X-ray examination room is made RF-quiet. MR imaging can then be performed. Afterwards, the magnet is removed from the room, the doors closed, and the X-ray equipment is returned to its working position.

The MR scanner is used to provide information complementary to that obtained using X-ray. It can be used, for example, to perform a baseline assessment prior to intervention as well as to perform a post-intervention assessment. Such an assessment may include perfusion and viability studies of, for example, the heart or of the brain.

As example workflows for the system, consider elective procedures and emergency cases, such as acute stroke or acute coronary syndromes.

In the Elective Procedure Workflow, a preliminary, baseline MR scan can be obtained with the patient either in the diagnostic room or in the angiography room; this is basically a pre-procedure MR scan. The objective is to measure baseline parameters that are clinically relevant. For a cardiac procedure, this may include baseline cardiac function and myocardial viability.

After the MR scan, the patient is transferred to the angiography room if MR imaged in the diagnostic room, or simply remains on the table if already in the Angio room, where coronary or cerebral angiography and angioplasty, followed by stent placement are conducted, if required, in the customary fashion under X-ray fluoroscopy.

The MR Scanner magnet enters the angiography room and acquires the appropriate MR images. After reviewing the MR data and possibly correlating with the X-Ray data, the interventionist can either discharge the patient or continue treatment.

In the emergency Case Workflow, the patient is admitted and undergoes preparation in the Emergency room (both groins shaved, screening for MR examination, metal check, etc.). The patient is brought to AR (in the case of an acute myocardial infarction diagnosed by ECG) and vascular access via the groin is established. MR Imaging could take place in the AR for baseline assessment in order to minimize movement of the acute patient. The scanner is brought into the AR for MR measurement of baseline cardiac function and perfusion imaging in a cardiac case. In the case of stroke, the MR images will reveal if interventional therapy is indicated. In both cases, MR baseline imaging is completed and processed in a minimum time period. In both stroke and cardiac patients angiography and intervention (angioplasty, thrombectomy, or delivery of clot-busting drugs at the site of occlusion) are performed in the customary fashion, under X-Ray fluoroscopy, if so indicated.

The MR Scanner is brought into the AR for subsequent MR images acquisition. After reviewing the MR images and possibly correlation with the X-ray data, the interventionist will discharge the patient or continue with treatment.

In the arrangement for moving the X-ray system as shown in FIG. 1 the MR enters the X-ray examination room and moves over the head end of the table 10. Since the path of the MR passes right through the location of the C-arm stands, the latter must be moved before the magnet may enter. Depending on need, a floor-mounted C-arm stand may be moved on floor rails, floor turntable, or a boom mounted on the floor or wall. Depending on need, a ceiling-mounted C-arm stand may be moved using extended rails to park it at the foot end of the table, by mounting the stand rails on a platform suspended from the movable magnet rails, or by fixing the stand rails on a platform with a telescopic arm to move them laterally.

Using a solution to move a floor-mounted stand together with a mover for a ceiling mounted stand provides a mechanism to move a biplane system. The mover can provide a mounting position of the single plane or biplane at some non-zero angle to the MR rails, e.g., 90 degrees.

The Patient Handling System or support table is shown in FIGS. 2 to 7 as indicated generally at 10. The patient support table includes a base 11 of a conventional construction which allows the base to move a patient support portion 12 to required locations in height and in orientation. Suitable drive mechanisms and couplings are known in the art and thus are not required to be described herein. At the top of the base 12 is mounted the patient support portion in the form of a generally planar body 12 formed of a fiber reinforced plastics material so as to define a surface area sufficient for supporting the patient while lying on the patient support portion. The patient support 12 includes a rear edge 13 at or beyond the feet of the prone patient together with two side edges 14 and 15 spaced by a distance sufficient to receive and contain the legs, body and arms of the patient to be supported by the support portion.

Figure 2:
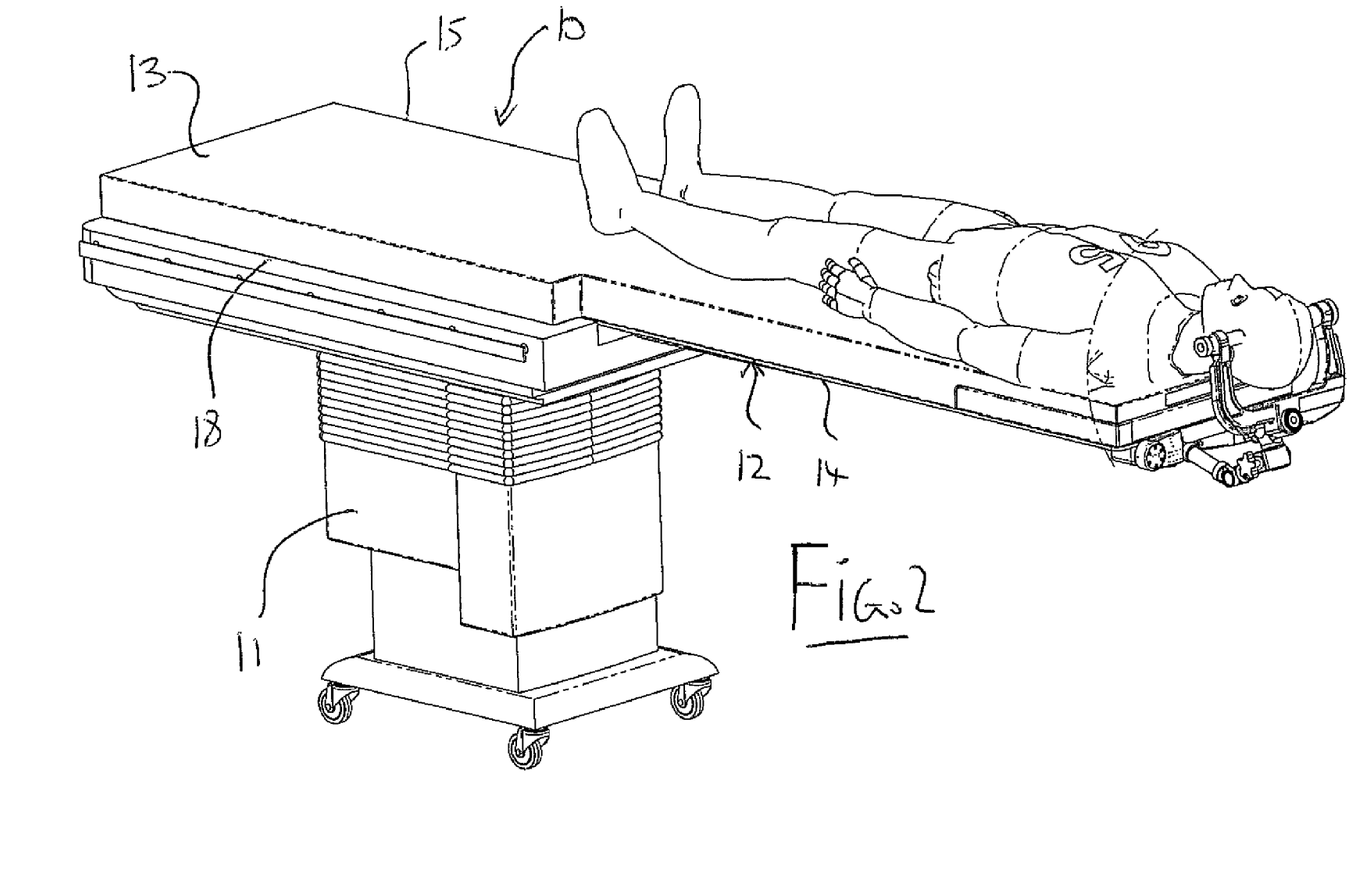
FIG. 2 is an isometric view of a table for mounting the patient, the base being omitted for convenience of illustration, and showing the a head clamp for the skull of the patient mounted on the table.

At a forward end 16 is provided a head clamp 20 for mounting and holding the head of the patient.

On top of the patient support portion 12 is provided a mattress 18 which is shaped to overlie the patient support portion 12.

The structural support for the patient is provided by the support portion 12 which is formed of a fiber reinforced resin material where the fibers are laid in sheets and infused by the resin material to provide a flat structural member of sufficient strength to carry the weight of the typical patient. In order that the patient support portion be formed of a material which does not interfere with the operation of the magnet or the generation and acquisition of the necessary signals used in magnetic resonance imaging, the fiber reinforcement selected for use in the structure of the portion 12 is a fiber which has sufficient strength to provide the necessary resistance to bending but a fiber which is non-electrically conductive. Thus carbon fibers cannot be used since long carbon fibers generate or allow currents to flow within the structure of the portion and such currents will interfere with the necessary signals. The currents are generated by the high magnetic fields within the magnet and by the electro magnetic signals which are generated within the magnet for use in the magnetic resonance imaging. Typically aramid fibers such as Kevlar (TM) can be used in replacement for the carbon fibers typically used in such structures.

The mattress is formed of a stiff foam material encased by a skin to provide an exterior surface which is resistant to fluids and can be readily cleaned for sterilization to be used in clinical situations.

The patient handling system thus contains the following key components: the patient table 11, the head holder 20, and MR imaging coils (not shown). The system, including integration of the key components, is specially designed to permit imaging with both MRI and X-ray imaging modalities, while maintaining sufficient image quality and workflow.

The patient table is designed to allow the patient to be scanned with both MR and X-ray imaging modalities. The patient table is comprised of two major components: the table pedestal and the tabletop. The tabletop is fully MR and X-ray compatible; the table pedestal does not adversely impact image quality during MR scanning (i.e. does not impact homogeneity of magnetic field), the pedestal also does not experience significant forces from the magnetic field. The tabletop is positioned so that the table pedestal (which is also not X-ray compatible) is at a distance that is sufficiently away from the imaging site. The tabletop integrates the head holder, arm boards and MR imaging coils.

The head holder supports the patient's head during the procedure and must also be MR and X-ray compatible. The head holder integrates into the patient table in a manner that is very efficient to position and remove. The MR imaging head coils may also be integrated with the head holder and are easily positioned and removed at the imaging site.

The MR imaging coils consist of head coils for imaging the head and upper spine. MR coils are not X-ray compatible and thus are positioned and removed from the imaging area when switching between imaging modalities without having to move or interfere with the patient.

During certain medical procedures, both X-ray and MR imaging modalities may be employed, at separate times during the procedure. Since MRI coils are not X-ray compatible, it is necessary to position and remove the coils quickly and easily when switching between MRI and X-ray imaging. For cases where it is necessary to keep the patient in a fixed position during the procedure, the imaging coils must also be positioned and removed without moving or shifting the patient in any way. For example, cranial procedures will employ the head holder to secure the head of the patient during the entire procedure. The MR imaging head coils will be easily positioned around the head holder without moving the head holder or the patient's head in any way.

The patient table consists of a table top that is completely MR and X-ray compatible. The tabletop also enables the integration of various MR imaging coils, such as head coils and cardiac coils, with the special feature of positioning and removing the coils without moving or shifting the patient in any way.

The tabletop also includes a means of easily positioning and removing the head holder; this includes a ridge or ledge around the head end of the tabletop, where the head holder may slide on with a dovetail interface. The imaging head coils also are integrated to the table in this fashion.

The head holder and table adapter assembly include the head holder that secures the head during the procedure and also a table adapter that secures the head holder to the patient table and also provides a means of adjusting the position/orientation of the head holder. The entire assembly is completely MR and X-ray compatible. There are various means of securing the patient's head, including a horseshoe head holder, a sling/suspender head holder, and a head cradle. The horseshoe head holder includes a rigid frame that is cushioned by gel, foam, or air inflated pillows; the sides and top of the patient's head may be supported by a strap or by side cushions. The frame may also be adjustable for accommodating a large range in head sizes. The sling/suspender head holder consists of soft material (e.g. fabric) that is shaped into a sling to support the back and sides of the head. The top of the head may be supported by a fabric strap; foam padding may insert between layers of material in the sides of the sling to cushion the head where the table adapter interfaces to the sling/suspender head holder. The head cradle is a scoop-shaped device that cradles the head and neck of the patient and includes foam or inflatable air pillows to cushion the back of the patient's head (for comfort) and also preventing the patient from moving the head from side to side. One additional feature of the inflatable pillow is that the pillow may be deflated to bring the head down slightly so that it is even closer to the portion of MR imaging head coil that is positioned directly underneath the head of the patient, which will increase MR image quality. The table adapter may interface to the head holder at various orientations, such as at the front of the head holder (closest to the patient's head), at the back of the head holder (furthest from patient table), along the sides of the head holder, or along the top of the head holder.

Figure 3:
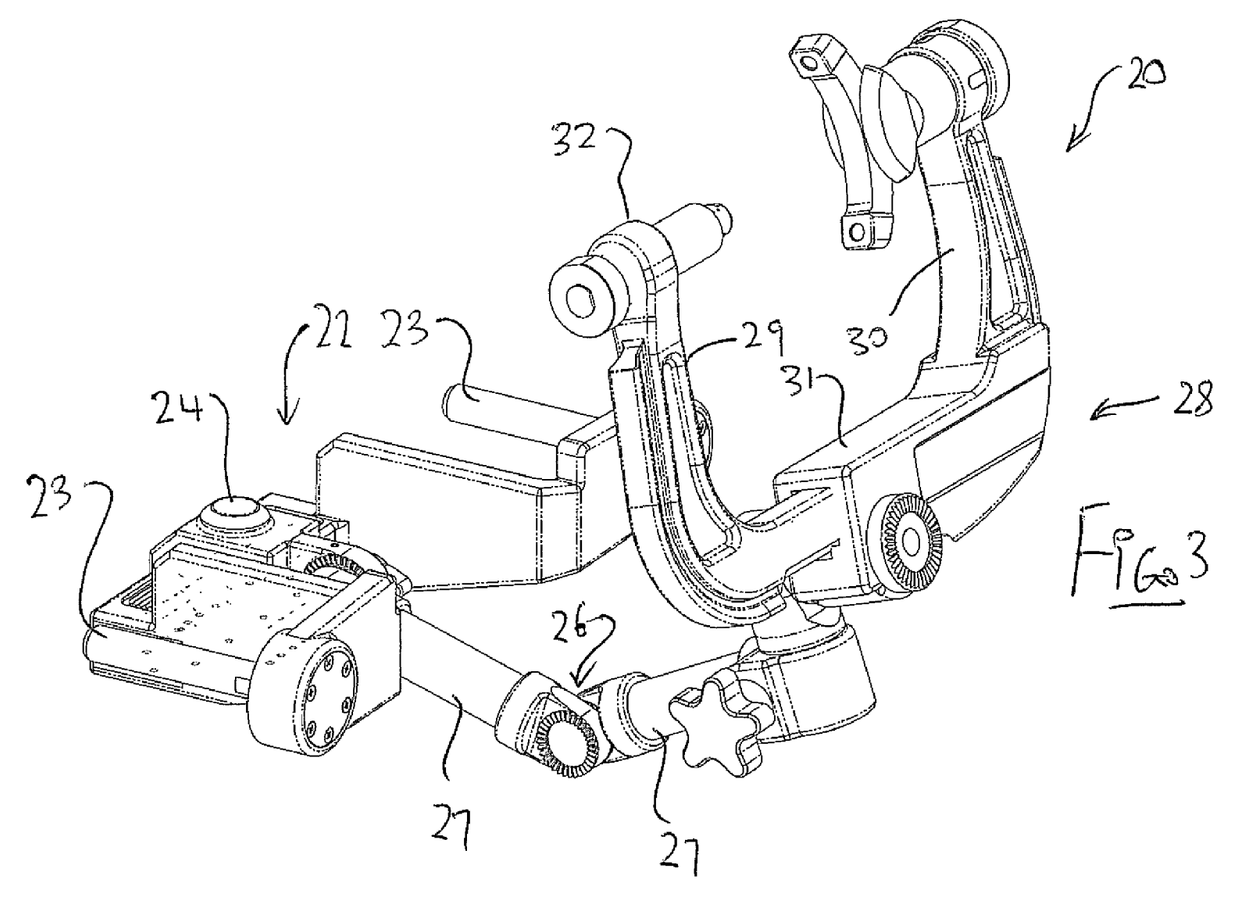
FIG. 3 is an isometric view on an enlarged scale of the head clamp of FIG. 2.

The head holder shown in FIGS. 2 and 3 is of a conventional design and includes a mounting portion 22 which is connected to the end face of the table 20 by two mounting pins 23. The mounting portion includes a central boss 24 which connects to and supports a link 25 formed by two arms 27 and a plurality of swivel connecting joints 26 which allow the head holder clamp 28 to be moved to different positions to mount the head at a required position. The clamp 28 includes a three point mounting carried on two arms 29 and 30 which can be adjusted in spacing by a rack 31. One of the mounting points is carried on a screw 32 to allow the clamp to engage the head as required.

The components for the head holder 20 are formed from the materials set out hereinafter. In many cases the parts are machined from a supply portion of the material. In other cases the parts are fabricated.

Figure 4:
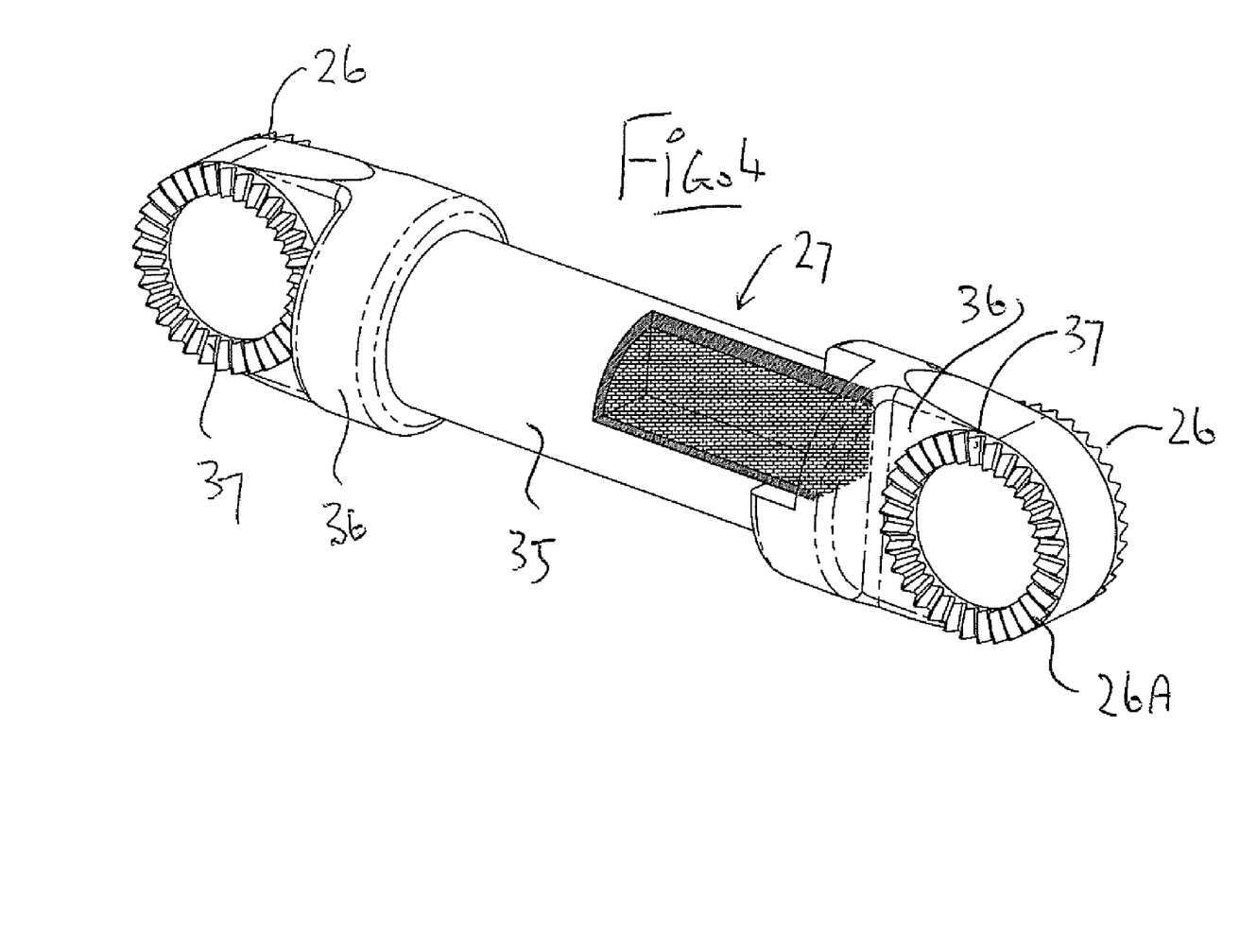
FIG. 4 is an isometric view on an enlarged scale of a portion of the head clamp of FIG. 3.

In FIG. 4 is shown one example of the parts concerned which is one of the arms 27 with the swivel couplings 26 at opposite ends. Each swivel coupling includes a circular toothed face 26A which matches with a corresponding face of a next part so that the parts can be rotated about a central axis to provide angular adjustment.

In the example shown in FIG. 4 the arm 27 is manufactured from a main elongate bar 35 which carries at its ends two end coupling portions 36. Each end coupling portion carries two disk portions 37 which define the circular toothed face 26A.

The end couplings 36 are formed of a material which is selected to provide a required strength and ability to be machined. One example of the material to be used is Garolite which is manufactured by under the code G10-FR4 (FR4). This is a fire rated electrical-grade, dielectric fiberglass laminate epoxy resin system combined with a glass fabric substrate. The abbreviation "FR4" means: F (for flame) and R (for retardancy) and the 4 is a #4 epoxy. FR4 grades offer excellent chemical resistance, flame ratings (UL94-VO) and electrical properties under dry and humid conditions. FR4 also features high flexural, impact, superior mechanical strength and bond strength at temperatures up to 130° C.

Other materials of the same characteristics can be selected which are epoxy resins reinforced by glass fibers. The use of glass fibers allows the finished product to be thinner than parts manufactured from other reinforcing fibers such as cotton which are conventionally believed to provide an improved reduction in Aluminum Equivalence Factor for use in the X-ray imaging but have been found to be unacceptable in MR imaging due to the creation of distortion and artifacts in the image.

The circular disks 37 are formed from polyphenylene sulphide mixed with non-woven random fibreglass. Polyphenylene sulphide (PPS) is a high performance semi-crystalline polymer that offers an excellent combination of thermal, mechanical and chemical resistance properties. Applications requiring high temperature stability, toughness and chemical resistance at elevated temperatures, are good candidates for Polyphenylene sulphide.

The bar 35 is formed from a composite of the polyurethane or polymethacrylimide foam enclosed by a layer of Aramid fibers. The polyurethane foam is a polymer consisting of a chain of organic units joined by (carbamate) links. Polyurethane polymers are formed by reacting a monomer containing at least two isocyanate functional groups with another monomer containing at least two alcohol groups in the presence of a catalyst.

Polymethacrylimide foam is produced by thermal expansion of a co-polymer sheet of methacrylic acid and methacrylonitrile. During the foaming process the copolymer sheet is converted to PMI-PolyMethacrylImide. Alcohol is used as a blowing agent. It has a very homogeneous cell structure and isotropic properties.

The foam core is machined to a required shape and inserts may be applied to provide fasteners. The machined foam part is then covered with a layer of a woven fabric formed from aramid fibers. Aramid fibers are a class of heat-resistant and strong synthetic fiber. They are fibers in which the chain molecules are highly oriented along the fiber axis, so the strength of the chemical bond can be exploited. The woven sheet is supplied embedded in a non-cured polymer which can be cured in a press after the covering layer or layers are wrapped around the foam core. The curing action bonds the layer to the core so as to provide a structural composite part of the required strength. It will be appreciated that this part cannot be machined once formed and hence the end couplings 36 are formed from a machinable material and fastened to the structural bar by screw fasteners (not shown) and epoxy.

Figure 5:
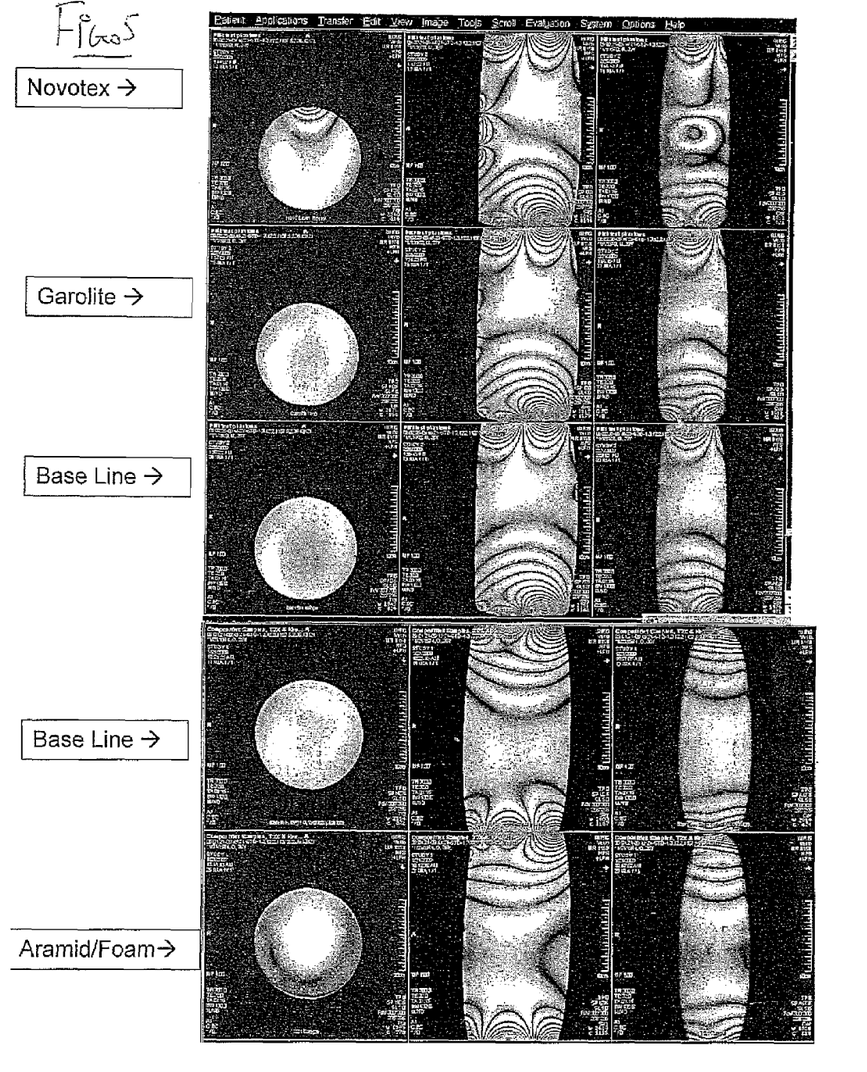
FIG. 5 is a series of images taken on an MR imaging system using components manufactured from different materials.

FIG. 5 shows a series of images taken in MR imaging which show a base line material together with the above materials in comparison with the base line material and the conventional Novotex.

This test procedure is used to validate compatibility of materials with MRI systems.

Tests are performed to verify that the material does not affect Signal to Noise Ratio (SNR)—The object under test must allow for measurements using the body scout. SNR cannot be compromised by more than 10% during body scout measurements.

The constant magnetic field homogeneity (BO). The object under the test should not cause any inhomogeneity of the magnetic field The RF field (gradient filed) distortions. The object under the test should not cause to any inhomogeneity of the RF field.

Not generate signals with a short echo time. Certain materials cause a MR-signal (i.e. plastics) with very short echo time. MR coils are very sensitive to this. Possible folding over artifacts can occur which could be mirrored into the region of interest. Therefore the test object should not create a MR signal.

The images obtained by the above materials are shown in FIG. 5 and illustrate that the Novotex product generates significant and unacceptable distortion of the image obtained during the MR imaging procedure whereas the materials defined above provide no such visible distortion.

The following table sets out the Aluminum Equivalence Factors for a number of material including the above materials in comparison with the conventional Novotex

| Material Type | G10/FR4 | PPS | Aramid/foam (1.6 mm skin/ 40 mm foam | Novotex |
|---|---|---|---|---|
| Al Equivalence per 10 mm thickness of material | 5 mm | 6 mm | 1.5 mm | 4 mm |

This procedure applies to estimate the X-ray attenuation of the test material, which is the only way to qualify the material in the numeric way, to be compatible as a part of international regulation bodies (FDA. IEC and etc) and to ensure that no harmful affect will be induced to the patient due to normal X-ray exposure.

Aluminum Equivalence is the thickness of type 1100 Aluminum that affords the same x-ray attenuation as the material to be tested. The attenuation must be measured with x-rays of a specified Beam Quality.

Beam Quality is a measure of the hardness (relative penetrating power) of an x-ray beam. It is specified by two numbers: (1) the x-ray tube voltage (kVp); and (2) the thickness of type 1100 Aluminum that reduces the exposure rate of the beam by one-half, known as the half-value layer (HVL).

For the purposes of IEC and FDA, Al equivalence is measured with a beam having a half-value layer of 3.7 mm at 100 kVp.

Thus the above part 27 defines a structural support component for use in imaging of a part of a patient using Magnetic Resonance and X-ray imaging where the structural support component is formed of one or more materials each of which has an Aluminum equivalence factor of less than 10 mm and preferably of the order of 5 to 5 mm.

As shown in FIG. 5, the structural support component is arranged such that the presence of the structural support component in an imaging zone of a magnetic resonance imaging system when generating the image does not generate any visually determinable distortion in the image.

The finished part should go thru complete X-ray test to determine the Al equivalence number and the level of visual interference of the MR image, if any.

While it is not essential in regard to all such parts depending on their construction and function, in most cases the component is formed of two or more different materials where the materials have different physical characteristics. Thus one of the materials used for the disk 37 is harder is and is used to form wear parts where two separate parts are butting. Also, one of the materials is more rigid is and is used to form elongate bars 35.

Preferably the component as shown at 35 is formed of three different materials where the materials have different physical characteristics, with the first material selected to form the elongate bar 36, the second material selected to form machined end portions 36 of the bar and the third material selected to form wear parts 37 attached to the end portions.

The invention claimed is:

1. Apparatus for use in imaging of a head of a patient using Magnetic Resonance and X-ray imaging comprising:
   a patient support table, the patient support table comprising;
      a table support base for mounting in a fixed position in an imaging suite;
      and an upper patient support portion on which the patient can lie with the part of the patient exposed for imaging;
      the upper patient support portion being mounted for controlled movement thereof relative to the table support base;
   a magnetic resonance imaging system for obtaining images of the part of the patient, the magnetic resonance imaging system comprising:
      a magnet for use with a control system for controlling and varying a magnetic field of the magnet;
      wherein the magnet is mounted on a magnet support arranged so that the magnet is movable between a magnetic resonance imaging position while the patient support portion remains supported on the table support base and a remote position in which the magnet is removed from the upper patient support portion by a distance such that the upper patient support portion is out of the magnetic field of the magnet;
   and an X-Ray imaging system comprising:

an X-Ray transmitter;

an X-Ray receiver;

the X-Ray source and the X-Ray receptor being arranged to define an imaging zone;

an X-Ray support base;

wherein the X-Ray imaging system is mounted for movement relative to the patient support table;

the patient table including a head holder for the head of the patient comprising:

a mounting portion for engaging an end of the upper patient support portion;

a head clamp having mounting points for engaging the head of the patient and an adjustment device for adjusting the spacing of the points;

an adjustment coupling for moving the head clamp to different positions on the mounting portion for moving the head of the patient to different positions;

the head holder and upper patient support portion being formed of one or more materials which are MR compatible;

the head holder and upper patient support portion being formed of one or more materials each of which has for a sample of 10 mm thickness an Aluminum equivalence factor of less than 10 mm;

the head holder and upper patient support portion being arranged such that the presence of the structural support component in an imaging zone of a magnetic resonance imaging system when generating the image does not generate any visually determinable distortion in the image.

2. The apparatus according to claim 1 wherein the head holder and upper patient support portion is formed of two different materials where the materials have different physical characteristics.

3. The apparatus according to claim 2 wherein one of the materials is harder and is used to form wear parts where two separate parts are butting.

4. The apparatus according to claim 2 wherein one of the materials is more rigid and is used to form elongate bars.

5. The apparatus according to claim 1 wherein the head holder and upper patient support portion is formed of three different materials where the materials have different physical characteristics, with a first material selected to form an elongate bar, a second material selected to form machined end portions of the bar and a third material selected to form wear parts attached to the end portions.

6. The apparatus according to claim 5 wherein one of the materials is an epoxy resin combined with a glass fiber substrate.

7. The apparatus according to claim 6 wherein said epoxy resin system combined with a glass fabric substrate is used for machined parts of the head holder and upper patient support portion.

8. The apparatus according to claim 5 wherein one of the materials is a polyphenylene sulphide with random fiber reinforcement using glass fibers.

9. The apparatus according to claim 8 wherein the polyphenylene sulphide with random fiber reinforcement using glass fibers is used to form wear parts.

10. The apparatus according to claim 5 wherein one of the materials is a polyurethane or Polymethacrylimide foam shaped to form a required member and covered on its outer surface with a layer formed from aramid fibers coated with a heat curable resin.

11. The apparatus according to claim 10 wherein the foam shaped covered on its outer surface with a layer formed from aramid fibers is used.

* * * * *